United States Patent [19]

Sturm et al.

[11] Patent Number: 4,610,716
[45] Date of Patent: Sep. 9, 1986

[54] FLUORINATED AZOLYL ETHANOL GROWTH REGULATORS AND MICROBICIDES

[76] Inventors: Elmar Sturm, Aesch; Urs Müller, Münchenstein; Hans Tobler, Allschwil, all of Switzerland

[73] Assignee: Ciba-Geigy Corporation Andsley, N.Y.

[21] Appl. No.: 558,140

[22] Filed: Dec. 5, 1983

[30] Foreign Application Priority Data

Dec. 14, 1982 [CH] Switzerland .................. 7270/82

[51] Int. Cl.$^4$ .................. A01N 43/50; A01N 43/653; C07D 233/60; C07D 249/08
[52] U.S. Cl. .......................................... 71/76; 71/92; 514/184; 514/383; 514/399; 548/101; 548/262; 548/341; 549/556; 568/308; 568/419
[58] Field of Search ............... 548/101, 262, 341; 424/245, 269, 273 R; 71/76, 92; 514/184, 383, 399

[56] References Cited

U.S. PATENT DOCUMENTS 4,359,470 11/1982 Kramer et al. ............... 548/262
4,382,944 5/1983 Kramer et al. ............... 548/262
4,428,949 1/1984 Kramer et al. ............... 548/101

FOREIGN PATENT DOCUMENTS 0061835 10/1982 European Pat. Off. .......... 548/262

OTHER PUBLICATIONS

Burger, Medicinal Chemistry (Second Edition, New York, 1960), p. 1055.

Primary Examiner—Alton D. Rollins
Attorney, Agent, or Firm—Edward McC. Roberts; Meredith C. Findlay

[57] ABSTRACT

The compounds described are those of the general formula I

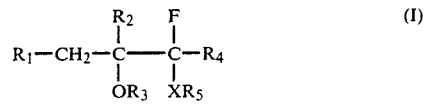

in which $R_1$ is an azolyl group; $R_2$ is $C_1$–$C_{12}$-alkyl; $R_3$ is hydrogen, $C_1$–$C_{12}$-alkyl, $C_2$–$C_4$-alkenyl or $C_2$–$C_4$-alkinyl, or benzyl which is unsubstituted or substituted by $C_1$–$C_6$-alkyl, $C_1$–$C_6$-alkoxy, $C_1$–$C_6$-haloalkyl, halogen and/or cyano; $R_4$ is hydrogen, fluorine or $C_1$–$C_6$-alkyl; $R_5$ is an unsubstituted or substituted radical chosen from the series comprising phenyl, naphthyl, biphenyl, benzylphenyl and benzyloxyphenyl, the substituents being chosen from the series comprising halogen, cyano, $C_1$–$C_6$-alkyl, $C_1$–$C_6$-alkoxy $C_1$–$C_6$-haloalkyl, $C_1$–$C_6$-alkylthio, $C_1$–$C_6$-haloalkoxy, $C_1$–$C_3$-haloalkylthio, nitro and/or thiocyano; and X is oxygen or sulfur; including the acid addition salts, quaternary azolium salts and metal complexes.

Methods for the preparation of these products are also disclosed, as well as agrochemical compositions containing one of these compounds as the active substance. A method of controlling phytopathogenic microorganisms and/or of regulating plant growth with the aid of these substances is furthermore described.

16 Claims, No Drawings

FLUORINATED AZOLYL ETHANOL GROWTH REGULATORS AND MICROBICIDES

The present invention relates to novel 1-fluoro-1-aryloxy-2-azolylmethyl-2-alkanol derivatives of the following formula I and acid addition salts, quaternary azolium salts and metal complexes thereof. It also relates to novel oxiranes of the following formula II. The invention furthermore relates to the preparation of these substances and to growth-regulating and microbicidal compositions containing at least one of these substances as the active substance. The invention also relates to the preparation of the above compositions and the use of the active substances or compositions for regulating plant growth and for controlling harmful microorganisms.

The compounds according to the invention are those of the general formula I

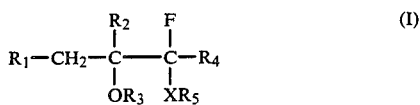

in which $R_1$ is an azolyl group; $R_2$ is $C_1$–$C_{12}$-alkyl; $R_3$ is hydrogen, $C_1$–$C_{12}$-alkyl, $C_2$–$C_4$-alkenyl or $C_2$–$C_4$-alkinyl, or benzyl which is unsubstituted or substituted by $C_1$–$C_6$-alkyl, $C_1$–$C_6$-alkoxy, $C_1$–$C_6$-haloalkyl, halogen and/or cyano; $R_4$ is hydrogen, fluorine or $C_1$–$C_6$-alkyl; $R_5$ is an unsubstituted or substituted radical chosen from the series comprising phenyl, naphthyl, biphenyl, benzylphenyl and benzyloxyphenyl, the substituents being chosen from the series comprising halogen, cyano, $C_1$–$C_6$-alkyl, $C_1$–$C_6$-alkoxy $C_1$–$C_6$-haloalkyl, $C_1$–$C_6$-alkylthio, $C_1$–$C_6$-haloalkoxy, $C_1$–$C_3$-haloalkylthio, nitro and/or thiocyano; and X is oxygen or sulfur; including the acid addition salts, quaternary azolium salts and metal complexes.

The expression azolyl preferably means a five-membered heterocyclic ring of aromatic character with nitrogen as the hetero-atom. Typical representatives are 1H-1,2,4-triazole, 4H-1,2,4-triazole and 1H-imidazole. The term alkyl by itself or as a constituent of another substituent is to be understood as meaning, for example, one of the following groups, depending on the stated number of carbon atoms: methyl, ethyl, propyl, butyl, pentyl, hexyl, heptyl, octyl, nonyl, decyl, undecyl, dodecyl and the like and their isomers, for example isopropyl, isobutyl, tert.-butyl, isopentyl and the like. Haloalkyl is a monohalogenated to perhalogenated alkyl substituent, for example $CHCl_2$, $CHF_2$, $CH_2Cl$, $CCl_3$, $CH_2F$, $CH_2CH_2Cl$, $CHBr_2$ and the like, preferably $CF_3$. Halogen here and in the following text is to be understood as meaning fluorine, chlorine, bromine or iodine, preferably fluorine, chlorine or bromine. Naphthyl is α- or β-naphthyl, preferably α-naphthyl. The expression haloalkoxy or haloalkylthio is an alkoxy or alkylthio radical, the haloalkyl moiety of which is as defined above under haloalkyl, alkenyl is, for example, prop-1-enyl, allyl, but-1-enyl, but-2-enyl or but-3-enyl, and alkinyl is, for example, propion-1-yl or propargyl. Aryl is, for example, naphthyl, in particular phenyl, and aralkyl is a $C_1$–$C_6$-alkyl radical, which is substituted by one of the above aryl groups. Thiocyano is —SCN.

The present invention thus relates to the free organic compounds of the formula I in the form of alcohols or ethers, and acid addition salts, quaternary azolium salts and metal complexes thereof. The free compounds, in particular the 1H-1,2,4-triazoles, are preferred.

Examples of salt-forming acids are inorganic acids, such as hydrogen halide acids, such as hydrofluoric acid, hydrochloric acid, hydrobromic acid or hydriodic acid, and sulfuric acid, phosphoric acid, phosphorous acid and nitric acid, and organic acids, such as acetic acid, trifluoroacetic acid, trichloroacetic acid, propionic acid, oxalic acid, formic acid, benzenesulfonic acid, p-toluenesulfonic acid or methanesulfonic acid.

Metal complexes of the formula I consist of the basic organic molecule and an inorganic or organic metal salt, for example the halides, nitrates, sulfates, phosphates, acetates, trifluoroacetates, trichloroacetates, propionates, tartrates, sulfonates, salicylates, benzoates and the like of the elements of the third and fourth main group, such as aluminium, tin or lead, and of the first to eighth sub-group, such as chromium, manganese, iron, cobalt, nickel, copper, zinc, silver, mercury and the like. The sub-group elements of the 4th period are preferred. The metals can be in the various valencies which are attributed to them. The metal complexes of the formula 1 can be mononuclear or polynuclear, i.e. they can contain one or more organic molecular moieties as ligands. Complexes with the metals copper, zinc, manganese and tin are preferred.

The compounds of the formula I are oils, resins or, in some cases, even solids which are stable at room temperature and which have very useful microbicidal and growth-regulating properties. They can be used preventively and curatively in the agricultural sector or related fields for controlling microorganisms which are harmful to plants and for regulating plant growth, the 1,2,4-triazol-1-ylmethyl derivatives in the context of the formula I being preferred. The active substances of the formula I according to the invention are distinguished by their very good tolerance by crop plants.

The following sub-groups are increasingly preferred, because of their pronounced growth-regulating and/or microbicidal action:

Compounds of the formula I in which $R_1$ is 1,2,4-triazole or imidazole; $R_2$ is $C_1$–$C_6$-alkyl; $R_3$ is hydrogen, $C_1$–$C_6$-alkyl, allyl, propargyl, benzyl, 2,6-dichlorobenzyl, 4-chlorobenzyl, 4-fluorobenzyl, 2,4-dichlorobenzyl or 2-chloro-4-fluorobenzyl; $R_4$ is hydrogen or methyl; $R_5$ is phenyl, 4-halophenyl or 2,4-dihalophenyl, or phenyl which is substituted by $CF_3$; and X is oxygen or sulfur.

Compounds of the formula I in which $R_1$ is 1,2,4-triazole; $R_2$ is tert.-butyl or iso-propyl; $R_3$ is hydrogen or $C_1$–$C_5$-alkyl; $R_4$ is hydrogen or methyl; $R_5$ is 4-halophenyl, 2,4-dihalophenyl or 4-$CF_3$—$C_6H_5$—; and X is oxygen.

Within the last group, the alcohols ($R_3$=H) are particularly preferred.

Examples of specific particularly preferred substances are: 1-fluoro-1-(4-chlorophenoxy)-2-(1H-1,2,4-triazol-1′-ylmethyl)-3,3-dimethyl-butan-2-ol, 1-fluoro-1-(4-fluorophenoxy)-2-(1H-1,2,4-triazol-1′-ylmethyl)-3,3-dimethyl-butan-2-ol, 1-fluoro-1-(2,4-dichlorophenoxy-2-(1H-1,2,4-triazol-1′-ylmethyl)-3,3-dimethyl-butan-2-ol and 1-fluoro-1-(4-chlorophenoxy-2-(1H-imidazol-1′-ylmethyl)-3,3-dimethyl-butan-2-ol.

The compounds of the formula I are prepared by a process which comprises first reacting an oxirane of the formula II

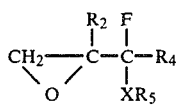

with an azole of the formula III $$M-R_1 \quad \text{(III)}$$

to give an alcohol of the formula Ia

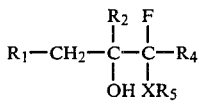

and, if an ether of the formula I is to be prepared, converting the alcohol of the formula Ia into an ether of the formula I in a conventional manner, for example by reaction with a compound of the formula IV $$R_3-W \quad \text{(IV)}$$

in which formulae Ia, II, III and IV, the substituents $R_1$ to $R_5$ are as defined under formula I, M is hydrogen or, preferably, a metal atom, in particular an alkali metal atom, such as Li, Na or K, Hal is halogen, in particular chlorine or bromine, and W is OH or a conventional leaving group, conventional group here and in the following text being understood as meaning a substituent, for example halogens: [such as fluorine, chlorine, bromine or iodine, preferably chlorine or bromine]; sulfonyloxy groups, preferably —OSO$_2$—R$_a$; acyloxy groups, preferably —OCO—R$_a$; and isourea radicals, preferably

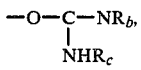

in which $R_a$, $R_b$ and $R_c$ independently of one another are $C_1$-$C_3$-alkyl or $C_1$-$C_3$-haloalkyl, or phenyl which is unsubstituted or substituted by halogen, methyl, nitro, trifluoromethyl and/or methoxy.

If appropriate, the reaction of II with III to give Ia is carried out in the presence of condensing agents or acid-binding agents. Suitable agents are organic and inorganic bases, for example tertiary amines, such as trialkylamines (trimethylamine, triethylamine, tripropylamine and the like), pyridine and pyridine bases (4-dimethylaminopyridine, 4-pyrrolidylaminopyridine and the like), oxides, hydrides, hydroxides, carbonates and bicarbonates of alkali metals and alkaline earth metals (CaO, BaO, NaOH, KOH, NaH, Ca(OH)$_2$, KHCO$_3$, NaHCO$_3$, Ca(HCO$_3$)$_2$, K$_2$CO$_3$ and Na$_2$CO$_3$), and alkali metal acetates, such as CH$_3$COONa or CH$_3$COOK. Moreover, alkali metal alcoholates, such as C$_2$H$_5$ONa, C$_3$H$_7$-nONa and the like, are also suitable. In some cases it may be advantageous first to convert the free azole III (M=hydrogen) into the corresponding salt, for example in situ with an alcoholate, and then to react the salt with the oxirane of the formula II in the presence of one of the above bases. In the preparation of the 1,2,4-triazolyl derivatives, 1,3,4-triazolyl isomers are in general also formed in a parallel reaction, and these can be separated from one another in a conventional manner, for example with different solvents.

The reaction (II with III to give Ia) is preferably carried out in an organic solvent which is relatively polar but inert in the reaction, for example N,N-dimethylformamide, N,N-dimethylacetamide, dimethylsulfoxide, acetonitrile, benzonitrile and others. Such solvents can be used in combination with other solvents which are inert in the reaction, for example benzene, toluene, xylene, hexane, petroleum ether, chlorobenzene, nitrobenzene and the like. The reaction temperatures are in a temperature range from 0° to 150° C., preferably 20° to 100° C.

This reaction (II with III to give Ia) can otherwise be carried out analogously to reactions which are already known between other oxiranes and azoles [cf. German Offenlegungsschrift No. 2,912,288].

The intermediates in the above part reactions can be isolated from the reaction medium and, if desired, purified by one of the generally customary methods, for example by washing, digestion, extraction, crystallisation, chromatography, distillation and the like, before the subsequent reaction.

In cases where W in formula IV is a conventional leaving group, the subsequent reaction of Ia to give I is carried out in the absence or, preferably, in the presence of a solvent which is inert in the reaction. Examples of suitable solvents are the following: N,N-dimethylformamide, N,N-dimethylacetamide, hexamethylphosphoric acid triamide, dimethylsulfoxide, 2-methyl-3-pentanone and the like. Mixtures of these solvents with one another or with other conventional inert organic solvents, for example with aromatic hydrocarbons, such as benzene, toluene, the xylenes and the like, can also be used. In some cases, it may prove to be advantageous to carry out the reaction in the presence of a base, for example an alkali metal hydride, hydroxide or carbonate, in order to accelerate the rate of reaction. However, it can also be advantageous first to convert the alcohol of the formula Ia (R$_3$=OH) into a suitable metal salt in a manner which is known per se, for example by reaction with a strong base.

Examples of suitable strong bases are alkali metal and alkaline earth metal hydrides (NaH, KH, CaH$_2$ and the like) and alkali metal-organic compounds, for example butyllithium or an alkali metal tert.-butoxide; alkali metal hydroxides, such as NaOH or KOH, can furthermore also be used if the reaction is carried out in an aqueous two-phase system in the presence of a phase transfer catalyst.

However, it is also possible first to convert the alcohol of the formula Ia into an alkali metal alcoholate in a conventional manner before the subsequent reaction, and then to react the alcoholate with a compound of the formula IV (in which W is a leaving group), the reaction advantageously being carried out in the presence of a crown ether. If M=K, 18-crown-6, in particular, is present; and if M=Na, 15-crown-5, in particular, is present. The reaction is advantageously carried out in a medium which is inert in the reaction. Examples of suitable solvents are ethers and ether-like compounds, for example di-lower alkyl ethers (diethyl ether, diisopropyl ether, tert.-butyl methyl ether and the like), tetrahydrofuran and dioxane, and aromatic hydrocarbons, such as benzene, toluene or the xylenes.

The following solvents are examples of the organic water-immiscible phase: aliphatic and aromatic hydrocarbons, such as pentane, hexane, cyclohexane, petroleum ether, ligroin, benzene, toluene, the xylenes and the like, halogenated hydrocarbons, such as methylene chloride, chloroform, carbon tetrachloride, ethylene dichloride, 1,2-dichloroethane, tetrachloroethylene and the like, and aliphatic ethers, such as diethyl ether, diisopropyl ether, t-butyl methyl ether and the like. Examples of suitable phase transfer catalysts are: tetraalkylammonium halides, bisulfates or hydroxides, such as tetrabutylammonium chloride, bromide or iodide; triethylbenzylammonium chloride or bromide; tetrapropylammonium chloride, bromide or iodide; and the like. Phosphonium salts are also suitable phase transfer catalysts. The reaction temperatures are in general between 30° and 130° C., or are the boiling point of the solvent or solvent mixture.

In cases where W in formula IV is a hydroxyl group, a condensation reaction is advantageously carried out. The two reactants are refluxed in a suitable solvent.

In principle solvents which are inert towards the reactants and, advantageously, form an azeotrope with water can be used here. Examples of suitable solvents here are aromatic hydrocarbons, such as benzene, toluene and the xylenes, or halogenated hydrocarbons, such as methylene chloride, chloroform, carbon tetrachloride, 1,2-dichloroethane, tetrachloroethylene and chlorobenzene, and also ether-like compounds, such as tert.-butyl methyl ether, dioxane and others. In some cases, the compound of the formula III itself can be used as the solvent. This condensation reaction is advantageously carried out in the presence of a strong acid, for example paratoluenesulfonic acid, at the boiling point of the azeotropic mixture.

To prepare the ethers of the formula I, it is also possible first to replace the free OH group in the compounds of the formula Ia by one of the above conventional leaving groups W and then to react the product with a compound of the formula IV (where W=OH)

The free hydroxyl group in the compounds of the formula Ia is preferably replaced by a leaving group W in a solvent which is inert in the reaction. Examples of such solvents are: aromatic and aliphatic hydrocarbons, such as benzene, toluene, the xylenes, petroleum ether, ligroin or cyclohexane; halogenated hydrocarbons, such as chlorobenzene, methylene chloride, ethylene chloride, chloroform, carbon tetrachloride or tetrachloroethylene; ethers and ether-like compounds, such as diethyl ether, diisopropyl ether, t-butyl methyl ether, dimethoxyethane, dioxane, tetrahydrofuran or anisole; esters, such as ethyl acetate, propyl acetate or butyl acetate; nitriles, such as acetonitrile; or compounds such as dimethylsulfoxide and dimethylformamide, and mixtures of such solvents with one another.

The leaving group W is introduced by conventional methods. If A is chlorine, phosphorus oxychloride, phosphorus trichloride, phosphorus pentachloride or, preferably, thionyl chloride, for example, is used as the reagent. The reaction is in general carried out at temperatures from 0° to +120° C. If W=bromine, phosphorus tribromide or phosphorus pentabromide is preferably used, and the reaction is carried out at 0° to +50° C. If W is one of the groups —OSO$_2$R$_a$, —OCO—R$_a$ or

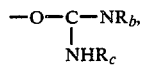

the corresponding acid chloride or amidino chloride is usually employed as the reagent. The reaction here is advantageously carried out at temperatures from −20° to +50° C., preferably −10° to +30° C., in the presence of a weak base, such as pyridine or triethylamine.

The starting substances of the formulae III and IV are generally known, or they can be prepared by methods which are known per se.

The oxiranes of the formula II are novel, and are intermediates which have been specially developed for the preparation of the useful active substances of the formula I. Because of their structural nature, they can be converted into the compounds of the formula I in a simple manner, and, moreover, some compounds of the formula II have a fungicidal activity against harmful fungi from the families of Ascomycetes, Basidiomycetes or *Fungi imperfecti.*

The oxiranes of the formula II can be prepared in a manner which is known per se, by reacting the ketones on which they are based, of the formula V

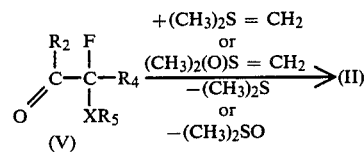

with dimethylsulfonium methylide, dimethyloxosulfonium methylide or with one of its salts, for example the methyliodide, in dimethylsulfoxide or another of the solvents described for the reaction of II with III. The substituents in formula V are as defined under formula I. The reaction is carried out at temperatures from 0° to 120° C.

Analogous reactions are known from the literature; compare JACS, 87, 1353 (1965). The reaction can in principle be carried out analogously to the reactions described therein. Ketones of the formula V can be prepared, for example, from the α-fluoro-α- halogeno-ketones, which are known per se, of the formula VI

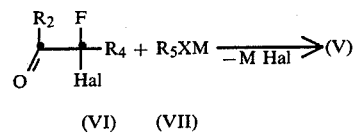

and compounds of the formula VII in conventional solvents which are inert in the reaction and, if appropriate, at elevated temperature. In the formulae VI and VII, the substituents R$_2$, R$_3$, R$_4$, R$_5$ and X are as defined under formula I, Hal is halogen, preferably chlorine or bromine, and M is preferably a metal atom, in particular sodium or potassium.

The compounds of the formula VII are known, or they can prepared by processes which are known per se.

Unless expressly specified in a particular case, one or more solvents or diluents which are inert in the reaction can be present in the preparation of all the starting substances, intermediates and end products mentioned here. Examples of suitable solvents or diluents are aliphatic and aromatic hydrocarbons, such as benzene, toluene, the xylenes and petroleum ether; halogenated hydrocarbons, such as chlorobenzene, methylene chloride, ethylene chloride, chloroform, carbon tetrachloride and tetrachloroethylene; ethers and ether-like compounds, such as dialkyl ethers (diethyl ether, diisopropyl ether, tert.-butyl methyl ether and the like), anisole, dioxane and tetrahydrofuran; nitriles, such as acetonitrile and propionitrile; N,N-dialkylated amides, such as dimethylformamide; dimethylsulfoxide; ketones, such as acetone, diethyl ketone and methyl ethyl ketone; and mixtures of such solvents with one another. In some cases, it may be advantageous to carry out the reaction or part steps of a reaction under a protective gas atmosphere and/or in absolute solvents. Suitable protective gases are inert gases, such as nitrogen, helium, argon or, in certain cases, also carbon dioxide.

The preparation process described, including all the part steps, is an important component of the present invention.

The compounds of the formula I

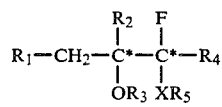

have in each case an asymmetric C-atom C* in the adjacent position to each of the substituents $OR_3$ and $XR_5$, and they can therefore exist in enantiomeric forms. In general, if $R_4$ is F, a mixture of two diastereomers is formed in the preparation of these substances. These can be separated from one another by physical methods (for example by crystallisation, chromatography or distillation). The enantiomers on which they are based can be split into the pure optical antipodes in a conventional manner, for example by fractional crystallisation of salts with strong optically active acids. The enantiomers or diastereomers can have different biological actions; thus, for example, the fungicidal action can be in the foreground in one form, and the plant-regulating action can be in the foreground in the other form. A gradual difference in activity may also occur in the same action spectrum.

The present invention relates to all the pure stereoisomers and enantiomers and mixtures thereof.

It has now been found, surprisingly, that the novel active substances of the formula I or compositions containing these active substances have the particular property that they interfere in plant metabolism in a controlled manner. This controlled interference in the physiological processes of plant development means that the active substances of the formula I can be used for various purposes, in particular for those linked with increasing the yield of useful plants, facilitating harvesting and saving labour by measures on plant crops.

In respect of the mode of action of plant growth regulators, experience gained hitherto has shown that an active substance can have one or several different actions on plants. The actions of the substances largely depend on the time of application relative to the stage of development of the seed or plant, and on the amount of active compounds applied to the plants or their environment and on the type of application. In all cases, growth regulators should have a positive influence on the crop plants in the desired manner.

Plant growth-regulating substances can be used, for example, to inhibit vegetative plant growth. Such an inhibition of growth is of economic interest, inter alia, in grasses, since, for example, the frequency of grass-cutting in ornamental gardens, parks and sports fields or at roadside verges can thereby be reduced. The inhibition of growth of herbaceous and woody plants at roadside verges and close to overland lines or quite generally in areas in which heavy growth is undesirable is also of importance.

The use of growth regulators to inhibit longitudinal growth in cereals is also important, since the danger of lodging of the plants before harvesting is reduced or eliminated completely by shortening the stem. In addition, growth regulators can strengthen the stem of cereals, which likewise counteracts lodging.

An inhibition in the vegetative growth permits denser planting of the crop in many crop plants, so that an increased yield, based on the area of soil, can be achieved.

A further mechanism of increasing the yield with growth inhibitors is based on the fact that a greater amount of nutrients is made available for blossom formation and fruit formation, whilst vegetative growth is restricted.

Promotion of vegetative growth can also frequently be achieved with growth regulators. This is of great utility if it is the vegetative parts of the plants which are harvested. Promoting the vegetative growth can, however, also simultaneously lead to a promotion of generative growth, so that, for example, more fruit or larger fruit is obtained.

Increases in yield can in some cases also be achieved by affecting the plant metabolism, without noticeable changes in vegetative growth. A change in the composition of the plants, which in turn can lead to a better quality of the harvested products, can furthermore be achieved with growth regulators. Thus it is possible, for example, to increase the sugar content in sugar beet, sugar cane, pineapples and citrus fruits or to increase the protein content in soybean or cereals.

Parthenocarpus fruit can be formed under the influence of growth regulators. Furthermore, the gender of the flowers can be influenced.

It is also possible favourably to influence the production or the efflux of secondary plant constituents with growth regulators. The stimulation of latex flux in rubber trees may be mentioned as an example.

Lateral branching by chemical breaking of the apical dominance can also be increased during the growth of the plant by using growth regulators. There is great interest in this action, for example, in the propagation of plants by cuttings. However, it is also possible to inhibit the growth of side shoots, for example to prevent the development of side shoots and hence to promote the growth of foliage of tobacco plants after decapitation.

The amount of leaf on plants can be controlled under the influence of growth regulators, so that defoliation of the plants at a desired point in time is achieved. Such defoliation is of interest in order to facilitate mechanical harvesting, for example of wine or cotton, or to reduce transpiration at a point in time at which the plants are to be transplanted. Premature shedding of fruit can be prevented by using growth regulators. However, it is also possible to promote shedding of fruit—for example in the case of fruit crops—up to a certain degree in the sense of chemical thinning out. Growth regulators can also be used to reduce the force required to detach the fruit from crop plants at the time of harvest, so that mechanical harvesting of the plants is permitted or manual harvesting is facilitated.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of the fruit. In addition, concentrating the ripening within a certain period of time is also achievable with the aid of growth regulators. This provides the preconditions for being able to carry out complete mechanical or manual harvesting in only a single path, for example in the case of tobacco, tomatoes or coffee.

Using growth regulators, it is furthermore possible to influence the latent period of seeds or buds of plants, that is to say the endogenous yearly rhythm, so that the plants, for example pineapples or ornamental plants in nurseries, germinate, shoot or blossom at a time at which they normally showed no readiness to do so.

Retardation of the shooting of buds or the germination of seeds can also be achieved with the aid of growth regulators, for example in order to avoid damage by late frosts in areas where frost is a hazard. On the other hand, it is possible to promote the root growth and/or to stimulate the development of shoots, so that growth can be restricted to a shorter period.

Growth regulators can also produce halophilicity in crop plants. This provides the preconditions for being able to cultivate plants on salt-containing soils.

Resistance of plants to frost and drought can also be induced with growth regulators.

Ageing (senescence) of plants or parts of plants can be inhibited or delayed under the influence of growth regulators. Such an action can be of great economic importance in that the storage stability of treated parts of plants or whole plants, such as fruit, berries, vegetables, lettuce or ornamental plants, after harvesting can be improved or lengthened. A considerable increase in yield can likewise be achieved, via extension of the photosynthetic activity phase, by treatment of crop plants.

Another important field of application for growth inhibitors is their use for inhibition of excessive growth in tropical cover crops. In tropical and subtropical single crop systems, for example in palm plantations, cotton fields, corn fields and the like, cover crops, especially varieties of leguminosae, are frequently planted beside the actual crop plants with the aim of maintaining or increasing the quality of the soil (prevention of drying out, supply of nitrogen) and of preventing erosion (removal by wind and water). The growth of these cover crops can now be controlled by application of the active substances according to the invention and the growth height of these cover crops can be kept at a low level, ensuring the crops thrive healthily and an advantageous soil structure is maintained.

It has furthermore been found, surprisingly, that the active substances of the formula I or corresponding compositions additionally contain, as well as advantageous growth-regulating properties, a microbicidal spectrum which is very advantageous for practical requirements. A further field of use of compounds of the formula I is therefore the control of harmful microorganisms, especially phytopathogenic fungi. Thus, the compounds of the formula I have a curative, preventive and systemic action, which is very advantageous for practical requirements, in protecting plants, especially crop plants, without having an adverse effect on these plants.

The microorganisms which occur on plants or parts of plants (fruit, blossom, foliage, stalks, tubers and roots) of various useful crops can be checked or destroyed with the active substances of the formula I, parts of plants which later additionally grow also remaining protected from such microorganisms.

The active substances are effective against the phytopathogenic fungi belonging to the following classes: Ascomycetes (for example Venturia, Podosphaera, Erysiphe, Monilinia and Uncinula); Basidiomycetes (for example the genera Hemileia, Rhizoctonia and Puccinia); and *Fungi imperfecti* (for example Botrytis, Helminthosporium, Fusarium, Septoria, Cercospora and Alternaria). The compounds of the formula I moreover have a systemic action. They can furthermore be used as dressing agents for the treatment of seed (fruit, tubers and seed) and plant seedlings, for protection from fungal infections and against phytopathogenic fungi which occur in the soil. The active substances according to the invention are distinguished by a particularly good plant tolerance.

The invention thus also relates to microbicidal agents and the use of the compounds of the formula I for the control of phytopathogenic microorganisms, especially fungi which are harmful to plants, and to the preventive avoidance of an attack on plants.

The present invention moreover relates to the preparation of agrochemical compositions, which comprises intimately mixing the active substance with one or more of the substances or groups of substances described herein. The invention also includes a method of treating plants which comprises applying the compounds of the formula I or the novel compositions.

In the context of this invention, examples of target crops for the fields of indication disclosed herein are the following varieties of plants: cereals: (wheat, barley, rye, oats, rice, sorghum and related plants); beet: (sugar beet and feed beet); pomaceous fruit, stone fruit and berry fruit: (apple, pear, plum, peach, almond, cherry, strawberry, raspberry and blackberry); pulses: (bean, lentil, pea and soybean); oil crops: (rape, mustard, opium, olive, sunflower, coconut, castor, cacao and groundnut); cucumber crops: (pumpkin, cucumber and melon); fibre crops: (cotton, flax, hemp and jute); citrus fruit: (orange, lemon, grapefruit and mandarin); vegetable varieties: (spinach, lettuce, asparagus, cabbage varieties, carrot, onion, tomato, potato and paprika); laural crops; (avocado, cinnamonum and camphor); and plants such as maize, tobacco, nut, coffee, sugar cane, tea, grape, hop and banana and natural rubber crops. In the context of the present invention, however, plants include all types of other green cover, whether ornamental plants (composites), grassed areas, embankments or general low cover crops which counteract erosion or drying out of the soil, or cover crops such as are desirable in tree and perennial crops (fruit plantations, hop crops, corn fields, vineyards and the like).

In the agricultural sector, active substances of the formula I are usually employed in the form of compositions, and can be applied to the area or plant to be treated at the same time as or after other active substances. These other active substances can be either fertilisers and trace element carriers, or other products which influence plant growth. They can, however, also be selective herbicides, insecticides, fungicides, bactericides, nematicides, molluscides or mixtures of these products, if appropriate together with further carriers, surfactants or other application-promoting adjuvants conventionally used in the art of formulation.

Suitable carriers and adjuvants can be solid or liquid and correspond to the substances conventionally used for this purpose in the art of formulation, for example natural or regenerated mineral substances, solvents, dispersants, wetting agents, tackifiers, thickeners, binders or fertilisers. Phospholipids are also advantageous formulation assistants.

A preferred method of applying an active substance of the formula I or an agrochemical composition containing at least one of these active substances is application to the foliage (leaf application). The number of applications depends on the threat of attack by the corresponding pathogen (type of fungus) or the way in which growth is influenced. However, the active substances of the formula I can also enter the plant through the root system via the soil (systemic action), by soaking the location of the plants with a liquid formulation or introducing the substances into the soil in solid form, for example in the form of granules (soil application). The compounds of the formula I can, however, also be applied to seeds (coating), either by soaking the seeds with a liquid formulation of the active substance or by coating them with a solid formulation. Moreover, other types of application are possible in particular cases, for example, controlled treatment of the plant stalks or of the buds.

The compounds of the formula I are thereby employed in unchanged form or, preferably, together with the assistants conventionally used in the art of formulation, and are thus processed in a known manner to, for example, emulsion concentrates, brushable pastes, directly sprayable or dilutable solutions, dilute emulsions, wettable powders, soluble powders, dusts or granules, by encapsulation in, for example, polymeric substances. The methods of application, such as spraying, misting, dusting, scattering, brushing or pouring, are chosen according to the intended aims and the given circumstances, as is the type of composition. Advantageous application amounts are generally 10 g to 5 kg of active substance (AS) per hectare; preferably 100 g to 2 kg of AS/hectare and in particular 200 g to 600 g of AS/hectare.

The formulations, i.e. the compositions, preparations or mixtures containing the active substance of the formula I and, where relevant, a solid or liquid adjuvant, are prepared in a known manner, for example by intimate mixing and/or grinding of the active substances with extenders, for example with solvents, solid carriers and, if appropriate, surface-active compounds (surfactants).

Suitable solvents are: aromatic hydrocarbons, preferably the fractions $C_8$ to $C_{12}$, for example xylene mixtures or substituted naphthalenes, phthalic acid esters, such as dibutyl phthalate or dioctyl phthalate, aliphatic hydrocarbons, such as cyclohexane or paraffins, alcohols and glycols, and ethers and esters thereof, such as ethanol, ethylene glycol and ethylene glycol monomethyl or monoethyl ether, ketones, such as cyclohexanone, strongly polar solvents, such as N-methyl-2-pyrrolidone, dimethylsulfoxide or dimethylformamide, and vegetable oils, which may or may not be epoxidised, such as epoxidised coconut oil or soybean oil; or water.

The solid carriers used, for example for dusts and dispersible powders, are as a rule ground natural minerals, such as calcite, talc, kaolin, montmorillonite or attapulgite. Highly disperse silicic acid or highly disperse absorbent polymers may also be added to improve the physical properties. Suitable granular adsorbent carriers for granules are porous types, for example pumice, broken brick, sepiolite or bentonite, and suitable non-absorbent carrier materials are, for example, calcite or sand. A large number of pregranulated materials of inorganic or organic nature, such as, in particular, dolomite or comminuted plant residues, can furthermore be used.

Suitable surface-active compounds are non-ionic, cationic and/or anionic surfactants with good emulsifying, dispersing and wetting properties, depending on the nature of the active substance of the formula I to be formulated. Surfactants are to be understood as also meaning mixtures of surfactants.

Suitable anionic surfactants can be either so called water-soluble soaps or water-soluble synthetic surface-active compounds.

Soaps are the alkali metal, alkaline earth metal or unsubstituted or substituted ammonium salts of higher fatty acids ($C_{10}$–$C_{22}$), for example the Na or K salts of oleic acid or stearic acid, or naturally occurring fatty acid mixtures, which can be obtained, for example, from coconut oil or tallow oil. Fatty acid methyl-laurin salts are also suitable.

However, so-called synthetic surfactants are more frequently used, in particular fatty sulfonates, fatty sulfates, sulfonated benzimidazole derivatives or alkylarylsulfonates.

The fatty sulfonates or sulfates are as a rule in the form of alkali metal, alkaline earth metal or unsubstituted or substituted ammonium salts and have an alkyl radical having 8 to 22 C atoms, alkyl also including the alkyl moiety of acyl radicals, for example the Na or Ca salt of ligninsulfonic acid, of dodecylsulfuric acid ester or of a fatty alcohol sulfate mixture prepared from naturally occurring fatty acid. These compounds also include the salts of sulfuric acid esters and sulfonic acids of fatty alcohol ethylene oxide adducts. The sulfonated benzimidazole derivatives preferably contain 2-sulfonic acid groups and a fatty acid radical having 8–22 C atoms. Examples of alkylaryl sulfonates are the Na, Ca or triethanolamine salts of dodecylbenzenesulfonic acid, dibutylnaphthalenesulfonic acid or a naphthalenesulfonic acid/formaldehyde condensate.

Corresponding phosphates, for example salts of the phosphoric acid ester of a p-nonylphenol-(4–14)-ethylene oxide adduct or phospholipids, are also suitable.

Particularly suitable non-ionic surfactants are polyglycol ether derivatives of aliphatic or cycloaliphatic alcohols, saturated or unsaturated fatty acids and alkyl phenols, which can contain 3 to 30 glycol ether groups and 8 to 20 carbon atoms in the (aliphatic) hydrocarbon radical and 6 to 18 carbon atoms in the alkyl radical of the alkylphenols.

Other suitable non-ionic surfactants are the water-soluble adducts, which contain 2 to 250 ethylene glycol ether groups and 10 to 100 propylene glycol ether groups, of polyethylene oxide and polypropylene glycol, ethylenediaminopolypropylene glycol and an alkylpolypropylene glycol having 1 to 10 carbon atoms in the alkyl chain. The compounds mentioned usually contain 1 to 5 ethylene glycol units per propylene glycol unit.

Examples of non-ionic surfactants are nonylphenol-polyethoxyethanols, castor oil polyglycol ether, polypropylene/polyethylene oxide adducts, tributylphenoxypolyethoxyethanol, polyethylene glycol and octylphenoxypolyethoxyethanol.

Fatty acid esters of polyoxyethylene sorbitan, such as polyoxyethylene sorbitan trioleate, are also suitable.

The cationic surfactants are, in particular, quaternary ammonium salts which contain at least one alkyl radical having 8 to 22 C atoms as an N-substituent and lower alkyl or benzyl radicals, which may or may not be halogenated, or lower hydroxyalkyl radicals as further substituents. The salts are preferably in the form of halides, methylsulfates or ethylsulfates, and are, for example, stearyltrimethylammonium chloride or benzyldi(2-chloroethyl)-ethylammonium bromide.

The surfactants conventionally used in the art of formulation are described, inter alia, in the following publications: "McCutcheon's Detergents and Emulsifiers Annual" MC Publishing Corp., Ridgewood, N.J., 1981; H. Stache, "Tensid-Taschenbuch" ("Surfactant Handbook"), 2nd Edition, C. Hanser Verlag, Munich, Vienna, 1981; and M. and J. Ash, "Encyclopedia of Surfactants", Volume I-III, Chemical Publishing Co., New York, 1980–1981.

The agrochemical formulations as a rule contain 0.1 to 99%, in particular 0.1 to 95%, of an active substance of the formula I and 99.9 to 1%, in particular 99.8 to 5%, of a solid or liquid additive, of which 0 to 25%, in particular 0.1 to 25%, is a surfactant.

Whilst concentrated compositions are more preferable as commercial goods, the end user as a rule employs dilute compositions.

The compositions can also contain other adjuvants, such as stabilisers, anti-foaming agents, viscosity regulators, binders, tackifiers and fertilisers or other active substances, in order to achieve specific effects.

Agrochemical compositions of this type are a component of the present invention.

The examples which follow serve to illustrate the invention in more detail, without restricting it. Temperatures are given in degrees Centigrade. Percentages and parts are by weight. RT is room temperature, h is hour, min is minute, DMSO is dimethylsulfoxide, THF is tetrahydrofuran and DMF is dimethylformamide.

EXAMPLE H1

(a) Preparation of the Intermediate

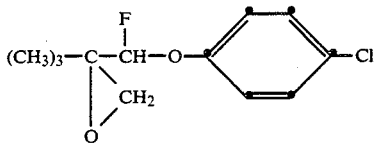

2-tert.-Butyl-2-[(4-chlorophenoxy)-fluoromethyl]-oxirane 43 g of trimethyloxosulfonium iodide were added in portions to a dispersion of 5.28 g of 80% sodium hydride in 300 ml of absolute DMSO under a nitrogen atmosphere, while stirring. When the exothermic reaction had subsided, the mixture was stirred for a further 1 h, a solution of 40 g of 1-(4-chlorophenoxy)-3,3-dimethyl-1-fluoro-2-butanone in 100 ml of THF was then added dropwise at RT and the mixture was stirred at RT for a further 2 h. The reaction solution was then poured onto ice-water and extracted several times with diethyl ether. The combined extracts were washed with water, dried over sodium sulfate and filtered and the filtrate was concentrated. Yield of crude product: 41.5 g in the form of a yellow-brown oil, which can be either purified by column chromatography or further processed without purification.

(b) Preparation of the End Product

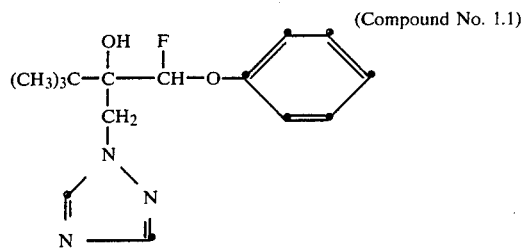

(Compound No. 1.1)

1-Fluoro-1-(4-chlorophenoxy)-2-(1H-1,2,4-triazol-1'-ylmethyl)-3,3-dimethyl-butan-2-ol 20.9 g of the 2-tert.-butyl-2-[(4-chlorophenoxy)-fluoromethyl]-oxirane prepared according to (a) were dissolved in 300 ml of DMF, and 8.3 g of 1,2,4-triazole and 0.9 g of potassium tert.-butanolate were added. The reaction mixture was stirred for 5 h and thereby warmed to 120° C., and was then cooled to RT, diluted with three times the of ice-water and extracted several times with diethyl ether. The combined extracts were washed with water, dried over sodium sulfate and filtered and the filtrate was concentrated. Yield: 23 g, in the form of a colourless oil.

The products below can also be prepared in a similar manner:

TABLE 1:

Compounds of the formula

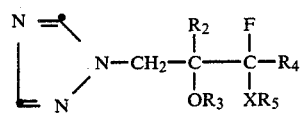

| Compound No. | R$_2$ | R$_3$ | R$_4$ | R$_5$ | X | Physical constant |
|---|---|---|---|---|---|---|
| 1.1 | t-Butyl | H | H | C$_6$H$_4$Cl(4) | O | n$_D^{50}$1.5223 |
| 1.2 | t-Butyl | H | H | C$_6$H$_4$F(4) | O | n$_D^{50}$1.5041 |
| 1.3 | t-Butyl | H | H | C$_6$H$_4$Br(4) | O | melting point 124–125° C. |
| 1.4 | t-Butyl | H | H | C$_6$H$_4$CH$_3$(4) | O | melting point 110–111° C. |
| 1.5 | t-Butyl | H | H | C$_6$H$_4$OCH$_3$(4) | O | melting point 94–95° C. |
| 1.6 | t-Butyl | H | H | C$_6$H$_4$OCF$_3$(4) | O | melting point 117–118° C. |
| 1.7 | t-Butyl | H | CH$_3$ | C$_6$H$_4$F(4) | O | |
| 1.8 | t-Butyl | H | C$_2$H$_5$ | C$_6$H$_4$F(4) | O | |
| 1.9 | t-Butyl | H | F | C$_6$H$_4$Cl(4) | O | |
| 1.10 | t-Butyl | H | H | C$_6$H$_4$OCHF$_2$(4) | O | |
| 1.11 | t-Butyl | H | H | C$_6$H$_3$Cl$_2$(2,4) | O | viscous oil |
| 1.12 | t-Butyl | H | CH$_3$ | C$_6$H$_4$Br(4) | O | |
| 1.13 | t-Butyl | H | H | C$_6$H$_4$Cl(4) | S | |
| 1.14 | t-Butyl | H | H | C$_6$H$_4$F(4) | S | |
| 1.15 | t-Butyl | H | H | C$_6$H$_4$CF$_3$(4) | O | melting point 125–127° C. |
| 1.16 | t-Butyl | H | H | C$_6$H$_3$Cl(2,3) | O | melting point 115–120° C. |
| 1.17 | t-Butyl | CH$_3$ | H | C$_6$H$_4$F(4) | O | |
| 1.18 | t-Butyl | CH$_3$ | H | C$_6$H$_4$Cl(4) | O | |
| 1.19 | t-Butyl | CH$_3$ | H | C$_6$H$_4$Br(4) | O | |
| 1.20 | t-Butyl | CH$_3$ | H | C$_6$H$_4$OCF$_3$(4) | O | |
| 1.21 | t-Butyl | Benzyl | H | C$_6$H$_4$CH$_3$(4) | O | |

TABLE 1:-continued

Compounds of the formula

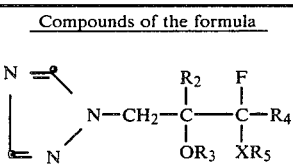

| Compound No. | R$_2$ | R$_3$ | R$_4$ | R$_5$ | X | Physical constant |
|---|---|---|---|---|---|---|
| 1.22 | t-Butyl | Benzyl | H | C$_6$H$_4$Cl(4) | O | |
| 1.23 | t-Butyl | Benzyl | H | C$_6$H$_4$CH$_3$(4) | O | |
| 1.24 | i-Propyl | H | H | C$_6$H$_4$F(4) | O | |
| 1.25 | i-Propyl | H | H | C$_6$H$_4$Cl(4) | O | |
| 1.26 | i-Propyl | H | H | C$_6$H$_5$ | O | |
| 1.27 | t-Butyl | H | H | C$_6$H$_5$ | O | |
| 1.28 | t-Butyl | CH$_3$ | H | C$_6$H$_5$ | O | |
| 1.29 | t-Butyl | CH$_3$ | CH$_3$ | C$_6$H$_4$F(4) | O | |
| 1.30 | t-Butyl | H | H | α-Naphthyl | O | |
| 1.31 | t-Butyl | H | H | C$_6$H$_4$—C$_6$H$_5$(4) | O | |
| 1.32 | t-Butyl | H | H | C$_6$H$_4$Cl(4) | O | melting point 119–120° C. |
| 1.33 | t-Butyl | H | H | C$_6$H$_3$(CH$_3$)$_2$(2,3) | O | Resin |

TABLE 2

Compounds of the formula

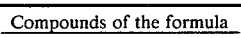

| Compound No. | R$_2$ | R$_3$ | R$_4$ | R$_5$ | X | Physical constant |
|---|---|---|---|---|---|---|
| 2.1 | t-Butyl | H | H | C$_6$H$_4$Cl(4) | O | n$_D^{50}$1.5311 |
| 2.2 | t-Butyl | H | H | C$_6$H$_4$F(4) | O | |
| 2.3 | t-Butyl | H | H | C$_6$H$_5$ | O | |
| 2.4 | t-Butyl | H | H | C$_6$H$_4$Br(4) | O | |
| 2.5 | t-Butyl | H | H | C$_6$H$_4$CH$_3$(4) | O | |
| 2.6 | t-Butyl | H | H | C$_6$H$_4$Cl(2) | O | |
| 2.7 | t-Butyl | H | H | C$_6$H$_4$CF$_3$(4) | O | |
| 2.8 | t-Butyl | H | H | C$_6$H$_4$OCF$_3$(4) | O | |
| 2.9 | t-Butyl | H | H | C$_6$H$_4$OCF$_2$H(4) | O | |
| 2.10 | i-Propyl | H | H | C$_6$H$_5$ | O | |
| 2.11 | i-Propyl | H | H | C$_6$H$_4$Cl(4) | O | |
| 2.12 | i-Propyl | H | H | C$_6$H$_4$F(4) | O | |
| 2.13 | t-Butyl | H | F | C$_6$H$_4$Cl(4) | O | n$_D^{50}$1.5136 |

Formulation examples for liquid active substances of the formula I (%=per cent by weight)

| F1. Emulsion concentrates | (a) | (b) | (c) |
|---|---|---|---|
| Active substance from the tables | 25% | 40% | 50% |
| Ca dodecylbenzenesulfonate | 5% | 8% | 6% |
| Castor oil polyethylene glycol ether (36 moles of ethylene oxide) | 5% | — | — |
| Tributylphenol-polyethylene glycol ether (30 moles of ethylene oxide) | — | 12% | 4% |
| Cyclohexanone | — | 15% | 20% |
| Xylene mixture | 65% | 25% | 20% |

Emulsions of any desired concentration can be prepared from such concentrates by dilution with water.

| F2. Solutions | (a) | (b) | (c) | (d) |
|---|---|---|---|---|
| Active substance from the tables | 80% | 10% | 5% | 95% |
| Ethylene glycol monomethyl ether | 20% | — | — | — |
| Polyethylene glycol MW 400 | — | 70% | — | — |
| N—Methyl-2-pyrrolidone | — | 20% | — | — |
| Epoxidised coconut oil | — | — | 1% | 5% |
| Benzine (boiling range 160–190° C.) | — | — | 94% | — |

(MW = molecular weight)

The solutions are suitable for use in the form of very small drops.

| F3. Granules | (a) | (b) |
|---|---|---|
| Active substance from the tables | 5% | 10% |
| Kaolin | 94% | — |
| Highly disperse silicic acid | 1% | — |
| Attapulgite | — | 90% |

The active substance is dissolved in methylene chloride, the solution is sprayed on to the carrier and the solvent is then evaporated off in vacuo.

| F4. Dusts | (a) | (b) |
|---|---|---|
| Active substance from the tables | 2% | 5% |
| Highly disperse silicic acid | 1% | 5% |
| Talc | 97% | — |
| Kaolin | — | 90% |

Ready-to-use dusts are obtained by intimate mixing of carriers with the active substance.

Formulation examples for solid active substances of the formula I (%=per cent by weight)

| F5. Wettable powders | (a) | (b) | (c) |
|---|---|---|---|
| Active substance from the tables | 25% | 50% | 75% |
| Na ligninsulfonate | 5% | 5% | — |
| Na lauryl-sulfate | 3% | — | 5% |
| Na diisobutylnaphthalenesulfonate | — | 6% | 10% |
| Octylphenol polyethylene glycol ether (7–8 moles of ethylene oxide) | — | 2% | — |
| Highly disperse silicic acid | 5% | 10% | 10% |
| Kaolin | 62% | 27% | — |

The active substance is mixed thoroughly with the adjuvants and the mixture is ground thoroughly in a suitable mill. Wettable powders which can be diluted with water to give suspensions of any desired concentration are obtained.

| F6. Emulsion concentrate | |
|---|---|
| Active substance from the tables | 10% |
| Octylphenol polyethylene glycol ether (4–5 moles of ethylene oxide) | 3% |
| Ca dodecylbenzenesulfonate | 3% |
| Castor oil polyglycol ether (35 moles of ethylene oxide) | 4% |
| Cyclohexanone | 30% |
| Xylene mixture | 50% |

Emulsions of any desired concentration can be prepared from this concentrate by dilution with water.

| F7. Dusts | (a) | (b) |
|---|---|---|
| Active substance from the tables | 5% | 8% |
| Talc | 95% | — |
| Kaolin | — | 92% |

Ready-to-use dusts are obtained by mixing the active substance with the carriers and grinding the mixture on a suitable mill.

| F8. Extruded granules | |
|---|---|
| Active substance from the tables | 10% |
| Na lignin-sulfonate | 2% |
| Carboxymethylcellulose | 1% |
| Kaolin | 87% |

The active substance is mixed with the adjuvants and the mixture is ground and moistened with water. This mixture is extruded and then dried in a stream of air.

| F9. Coated granules | |
|---|---|
| Active substance from the tables | 3% |
| Polyethylene glycol (MW 200) | 3% |
| Kaolin | 94% |

(MW = molecular weight)

The finely ground active substance is uniformly applied, in a mixer, to the kaolin, which has been moistened with polyethylene glycol. Dust-free coated granules are obtained in this manner.

| F10. Suspension concentrate | |
|---|---|
| Active substance from the tables | 40% |
| Ethylene glycol | 10% |
| Nonylphenol polyethylene glycol ether (15 moles of ethylene oxide) | 6% |
| Na lignin-sulfonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The finely ground active substance is intimately mixe with the adjuvants. A suspension concentrate is thus obtained, from which suspensions of any desired concentration can be prepared by dilution with water.

BIOLOGICAL EXAMPLES

EXAMPLE B1

Action against *Puccinia graminis* on wheat (a) Residual-protective action 6 days after sowing, wheat plants were sprayed with a spray liquor (0.002% of active substance) prepared from a wettable powder of the active substance. After 24 hours, the treated plants were infected with a uredospore suspension of the fungus. After incubation at 95–100% relative atmospheric humidity at about 20° C. for 48 hours, the infected plants were placed in a greenhouse at about 22° C. The development of rust pustules was evaluated 12 days after the infection.

(b) Systemic action 5 days after sowing, wheat plants were watered with a spray liquor (0.006% of active substance, based on the volume of soil) prepared from a wettable powder of the active substance. After 48 hours, the treated plants were infected with a uredospore suspension of the fungus. After incubation at 95–100% relative atmospheric humidity at about 20° C. for 48 hours, the infected plants were placed in a greenhouse at about 22° C. The development of rust pustules was evaluated 12 days after the infection.

Compounds from Tables 1 and 2 had a very good action against Puccinia fungi. Untreated but infected control plants showed a Puccinia attack of 100%. Inter alia, compounds 1.1, 1.2, 1.11 and 2.1 inhibited the Puccinia attack to 0 to 5%.

EXAMPLE B1

Action against *Cercospora arachidicola* on groundnut plants

Residual-protective action

Groundnut plants 10–15 cm high were sprayed with a spray liquor (0.006% of acti substance) prepared from a wettable powder of the active substance, and 48 hours later were infected with a conidia suspension of the fungus. The infected plants were incubated at about 21° C. at high atmospheric humidity for 72 hours and were then placed in a greenhouse until the typical leaf spots appeared. The fungicidal action was evaluated 12 days after the infection and was based on the number and size of the spots which appeared.

In comparison with untreated but infected control plants (number and size of spots=100%), groundnut plants which were treated with active compounds from the tables showed a greatly reduced Cercospora attack. Thus, compounds 1.1, 1.2 and 2.1 almost completely prevented the appearance of spots in the above experiments (0–10%).

EXAMPLE B3

Action against *Erysiphe graminis* on barley (a) Residual-protective action

Barley plants about 8 cm high were sprayed with a spray liquor (0.002% of active substance) prepared from a wettable powder of the active substance. After 3–4 hours, the treated plants were dusted with conidia of the fungus. The infected barley plants were placed in a greenhouse at about 22° C. and the fungal attack was evaluated after 10 days.

(b) Systemic action

Barley plants about 8 cm high were watered with a spray liquor (0.0006% of active substance, based on the volume of soil) prepared from a wettable powder of the active substance. Care was taken that the spray liquor did not come into contact with the above-ground parts of the plants. After 48 hours, the treated plants were dusted with conidia of the fungus. The infected barley plants were placed in a greenhouse at about 22° C. and the fungal attack was evaluated after 10 days.

Compounds of the formula I had a good action against Erysiphe fungi. Untreated but infected control plants showed an Erysiphe attack of 100%. Amongst other compounds from Tables 1 and 2, compounds Nos. 1.1, 1.2, 1.11 and 2.1 inhibited the fungal attack on barley to 0 to 5%.

EXAMPLE B4

Residual-protective action against *Venturia inaequalis* on apple shoots

Apple seedlings with fresh shoots 10–20 cm long were sprayed with a spray liquor (0.006% of active substance) prepared from a wettable powder of the active substance. After 24 hours, the treated plants were infected with a conidia suspension of the fungus. The plants were then incubated at 90–100% relative atmospheric humidity for 5 days and placed in a greenhouse at 20°–24° C. for a further 10 days. The scab attack was evaluated 15 days after the infection. Compounds 1.1, 1.2, 2.1 and others inhibited the disease attack to less than 20%. Untreated but infected shoots showed a 100% Venturia attack.

EXAMPLE B5

Action against *Botrytis cinerea* on apples

Residual-protective action

Artificially damaged apples were treated by dropping a spray liquor (0.02% of active substance) prepared from a wettable powder of the active substance onto the damaged sites. The treated fruits were then inoculated with a spore suspension of *Botrytis cinerea* and were incubated at a high atmospheric humidity at about 20° C. for one week.

The presence and size of the rot spots on the fruit served for evaluation of the fungicidal activity. On treatment with compounds from Tables 1 and 2, for example Nos. 1.1, 1.2 and 2.1, no rot sites or almost no rot sites (0–5% attack) were observed.

EXAMPLE B6

Inhibition of the growth of cereals

The cereal varieties *Hordeum vulgare* (summer barley) and Secale (summer rye) were sown in plastic pots containing sterilised soil in a greenhouse and were watered as required. About 21 days after sowing, the shoots were sprayed with an aqueous spray liquor of an active substance of the formula I. The amount of active substance, when converted, was 0.3, 0.5, 1.0, 2.5 and 3.0 kg of active substance per hectare. The growth of the cereal was evaluated 21 days after the application. It was possible to show that cereal plants which had been treated with active substances of the formula I show a great reduction in growth in comparison with untreated control plants. Compounds from Tables 1 and 2 proved to be particularly effective.

Test results:
Growth height of the cereal plants in % of the growth height of untreated control plants

| Compound No. | 3 kg of AS/hectare | | 2.5 kg of AS/hectare | | 1.0 kg of AS/hectare | | 0.5 kg of AS/hectare | | 0.3 kg of AS/hectare | |
|---|---|---|---|---|---|---|---|---|---|---|
| | Rye | Barley | Rye | Barley | Rye | Barley | Rye | Barley | Rye | Barley |
| 1.1 | — | — | 39 | 11 | — | — | 61 | 32 | — | — |
| 1.2 | — | — | 20 | 16 | — | — | 20 | 33 | — | — |
| 1.11 | 65 | 54 | — | — | 84 | 85 | — | — | 88 | 87 |
| 2.1 | — | — | 83 | 74 | — | — | 94 | 100 | — | — |

EXAMPLE B7

Inhibition of growth of grasses

The grasses *Lolium perenne, Poa pratensis, Festuca orina* and *Cynodon dactylon* were sown in plastic dishes with a soil/peat/sand mixture (6:3:1) in a greenhouse and were watered as required. The grasses which emerged were cut back to a height of 4 cm each week and, about 50 days after sowing and one day after the last cut, were sprayed with an aqueous spray liquor of an active substance of the formula I. When converted, the amount of active substance was 0.3, 0.5, 1.0, 2.5 or 3.0 kg of active substance per hectare. The growth of the grasses was evaluated 21 days after the application, and it was thereby found that the active substances, according to the invention, from Tables 1 and 2 caused a noticeable inhibition of growth.

Test results:
Growth height of grasses in percent of the growth height of the untreated control plants@

| Compound No. | 3 kg of AS/ hectare | 2.5 kg of AS/ hectare | 1.0 kg of AS/ hectare | 0.5 kg of AS/ hectare | 0.3 kg of AS/ hectare |
|---|---|---|---|---|---|
| 1.1 | — | 31 | — | 56 | — |
| 1.2 | — | 26 | — | 31 | — |
| 1.11 | 52 | — | 56 | — | 92 |
| 2.1 | — | 54 | — | 94 | —@ |

EXAMPLE B8

Increase in yield of soybean

Soybean of the "Hark" variety was sowed in plastic containers with a soil/peat/sand mixture in the ratio 6:3:1, and the containers were placed in a climatically controlled chamber. By optimum choice of temperature, illumination, addition of fertiliser and watering, the plants developed to the 5–6 trefoil leaf stage after about 5 weeks. At this point in time, the plants were sprayed with an aqueous liquor of an active substance of the formula I, until they were thoroughly wetted. The concentration of active substance was up to 500 ppm of active substance. Evaluation was carried out about 5 weeks after application of the active substance. In comparison with untreated control plants, the active substances of the formula I according to the invention caused a noticeable increase in the number and weight of crops harvested. Compounds from Tables 1 and 2 proved to be particularly effective.

EXAMPLE B9

Inhibition of growth of cover crops

Test plants of the *Centrosema plumieri* and *Centrosema pubescens* variety are grown from seedlings in plastic dishes with a soil/peat/sand mixture (1:1:1). After rooting, the small plants are reported in 9 cm pots and watered as required. The plants are further grown in a greenhouse at a day time temperature of 27° C. and a night time temperature of 21° C., at an average period of light of 14 hours (6,000 Lux) and at atmospheric humidity of 70%. The test plants are cut back to a height of about 15 cm and, 7 days after being cut back, are sprayed with a spray liquor of the active substance (when converted, 0.3, 1.0 or 3 kg of active substance per hectare). The growth of the treated plants is compared with that of pruned but untreated crop plants 4 weeks after the application. It can hereby be shown that compounds from Table 1 cause significant inhibition of growth of the cover crops.

Test results:
Growth height of cover crop plants in percent of the growth height of untreated control plants.

| Compound No. | Centrosema pubescens kg of AS/hectare | | | Psophocarpus palustris kg of AS/hectare | | |
|---|---|---|---|---|---|---|
| | 3.0 | 1.0 | 0.3 | 3.0 | 1.0 | 0.3 |
| 1.1 | 10 | 20 | 10 | 10 | 10 | 30 |
| 1.2 | 10 | 10 | 10 | 10 | 10 | 40 |
| 1.11 | 10 | 20 | 50 | 10 | 40 | 60 |

EXAMPLE B10

Inhibition of senescence in cereal plants

Summer wheat of the "Svenno" variety is sown in pots with compost soil and grown without specific climatic conditions, in a greenhouse. About 10 days after emergence, primary leaves 10 to 12 cm long are cut off and are placed individually in test tubes with 10 ml of an active substance suspension (1.25 to 10 ppm of active substance). The test tubes are placed in a climatically controlled room at 23° C. and 70% atmospheric humidity and are irradiated for on average 14 hours daily (10,000 Lux). The inhibition of senescence is evaluated 7 days after the leaves had been taken, by comparing the degree of yellowing in relation to green leaves which are still fresh. In this experiment, it can be observed that compounds from Tables 1 and 2 cause a significant inhibition of the senescence of the test plants.

EXAMPLE B11

Inhibition of the vegetative growth of soybean

Soybean of the variety "Hark" was sown in plastic pots with a soil/peat/sand mixture in the ratio 6:3:1 and the pots were placed in a greenhouse and watered as required. 15 days after sowing, the plants are sprayed with an aqueous spray liquor of an active substance of the formula I until they are wetted. When converted, the active substance combination is 0.1, 0.5 or 1.5 kg of active substance per hectare. The growth of the plants is evaluated 14 days after the application. It is thereby found that the active substances, according to the invention, from Tables 1 and 2 cause a noticeable inhibition of growth.

Test results:
Growth height of soya plants in percent of the growth height of untreated control plants

| Compound No. | 1.5 kg of AS/hectare | 0.5 kg of AS/hectare | 0.1 kg of AS/hectare |
|---|---|---|---|
| 1.1 | 8 | 8 | 16 |
| 1.2 | 9 | 14 | 68 |
| 1.11 | 18 | 24 | 24 |
| 2.1 | 79 | 83 | 92 |

What is claimed is:

1. A compound of the formula $$R_1-CH_2-\underset{\underset{OR_3}{|}}{\overset{\overset{R_2}{|}}{C}}-\underset{\underset{XR_5}{|}}{\overset{\overset{F}{|}}{C}}-R_4$$

in which $R_1$ is an azolyl group selected from the group consisting of 1,2,4-triazol-1-yl, 1,2,4-triazol-4-yl and imidazol-1-yl; $R_2$ is $C_1$-$C_{12}$-alkyl; $R_3$ is hydrogen, $C_1$-$C_{12}$-alkyl, $C_2$-$C_4$-alkenyl or $C_2$-$C_4$-alkynyl, or benzyl which is unsubstituted or substituted by $C_1$-$C_6$-alkyl, $C_1$-$C_6$-alkoxy, $C_1$-$C_6$-haloalkyl, halogen or cyano; $R_4$ is hydrogen, fluorine or $C_1$-$C_6$-alkyl; $R_5$ is an unsubstituted or substituted radical chosen from the series consisting of phenyl, naphthyl, biphenyl, benzylphenyl and benzyloxyphenyl, the substituents being chosen from the series consisting of halogen, cyano, $C_1$-$C_6$-alkyl, $C_1$-$C_6$-alkoxy, $C_1$-$C_6$-haloalkyl, $C_1$-$C_6$-alkylthio, $C_1$-$C_6$-haloalkoxy, $C_1$-$C_3$-haloalkylthio, nitro or thiocyano; and X is oxygen or sulfur; including an acid addition salt, quaternary azolium salt or metal complex.

2. A compound of claim 1, in which $R_1$ is 1,2,4-triazolyl or imidazolyl; $R_2$ is $C_1$-$C_6$-alkyl; $R_3$ is hydrogen, $C_1$-$C_6$-alkyl, allyl, propargyl, benzyl, 2,6-dichlorobenzyl, 4-chlorobenzyl, 4-fluorobenzyl, 2,4-dichlorobenzyl or 2-chloro-4-fluorobenzyl; $R_4$ is hydrogen or methyl; $R_5$ is phenyl, 4-halophenyl or 2,4-dihalophenyl, or phenyl which is substituted by $CF_3$; and X is oxygen or sulfur.

3. A compound of claim 2, in which $R_1$ is 1,2,4-triazolyl; $R_2$ is tert.-butyl or isopropyl; $R_3$ is hydrogen or $C_1$-$C_5$-alkyl; $R_4$ is hydrogen or methyl; $R_5$ is 4-halophenyl, 2,4-dihalophenyl or 4-$CF_3$—$C_6H_4$—; and X is oxygen.

4. A compound of claim 3, in which $R_3$ is hydrogen.

5. A compound of claim 1, selected from the series: 1-fluoro-1-(4-chlorophenoxy)-2-(1H-1,2,4-triazol-1'-ylmethyl)-3,3-dimethyl-butan-2-ol, 1-fluoro-1-(4-fluorophenoxy-2-(1H-1,2,4-triazol-1'-ylmethyl)-3,3-dimethylbutan-2-ol, 1-fluoro-1-(4-chlorophenoxy)-2-(1H-imidazol-1'-ylmethyl)-3,3-dimethyl butan-2-ol and 1-fluoro-1-(2,4-dichlorophenoxy)2-(1H-1,2,4-triazol-1'-ylmethyl)-3,3-dimethylbutan-2-ol.

6. A composition for the control of or prevention of attack by microorganisms or for regulating plant growth, which contains a compound of claim 1 in an amount effective to provide said control, prevention or regulation and a carrier.

7. A method of controlling or preventing attack of crop plants by phytopathogenic microorganisms or for regulating plant growth, which comprises applying a compound of claim 1 to the plants or their location in an amount effective to provide said control, prevention or regulation.

8. A method of claim 7, wherein the microorganisms are phytopathogenic fungi.

9. A method of claim 8 wherein the fungi are of the classes Ascomycetes, Basidiomycetes or *Fungi imperfecti*.

10. A method of claim 7 for growth inhibition to shorten the stem in cereal varieties to increase the resistance to breaking.

11. A method of claim 10, wherein the cereal varieties are oats, wheat, barley or rye.

12. A method of claim 7 for inhibition of the growth of grasses.

13. A method of claim 7 for inhibition of the growth of cover crops.

14. A method of claim 7 for regulating the growth of leguminosae to increase the yield.

15. A method of claim 14, wherein the leguminosa is soybean.

16. A method of claim 14 for increasing the yield by inhibition of senescence in cereals, soybean and cotton.

* * * * *